United States Patent [19]

Buzby, Jr.

[11] Patent Number: 4,520,205

[45] Date of Patent: May 28, 1985

[54] CHEMICAL RESOLUTION OF (+)-2,3-DIHYDROINDOLE-2-CARBOXYLIC ACID

[75] Inventor: George C. Buzby, Jr., Blue Bell, Pa.

[73] Assignee: American Home Products Corporation, New York, N.Y.

[21] Appl. No.: 578,320

[22] Filed: Feb. 10, 1984

Related U.S. Application Data

[63] Continuation of Ser. No. 392,916, Jun. 28, 1982, abandoned.

[51] Int. Cl.$^3$ ............................................. C07D 209/12
[52] U.S. Cl. ............................................. 548/491
[58] Field of Search ............................................. 548/491

[56] References Cited

U.S. PATENT DOCUMENTS 3,780,062 12/1973 Kaiser et al. ............................ 548/491
4,374,847 2/1983 Gruenfeld ............................... 548/491

FOREIGN PATENT DOCUMENTS 2086390 5/1982 United Kingdom .

OTHER PUBLICATIONS

Derwent Abstract No. 53434E/26 of Japanese Patent Publication J5 7081-462, published 5/21/82, (to Mochida Pharm.).

Vincent et al., Tetrahedron Letters, vol. 23, No. 16, pp. 1677–1680, (May, 1982).

*Primary Examiner*—Donald G. Daus
*Assistant Examiner*—S. A. Gibson
*Attorney, Agent, or Firm*—Arthur G. Seifert

[57] ABSTRACT

Described herein is a process for separating the enantiomers of (+)-2,3-dihydroindole-2-carboxylic acid, which process utilizes (+) or (−)-ephedrine as the resolving agent. The resolved acids are useful as intermediates in the preparation of angiotensin converting enzyme inhibitors.

4 Claims, No Drawings

CHEMICAL RESOLUTION OF (+)-2,3-DIHYDROINDOLE-2-CARBOXYLIC ACID

This is a continuation of application Ser. No. 392,916, filed June 28, 1982, now abandoned.

The invention for which patent protection is sought is a process for the separation of the optical enantiomers of (+)-dihydroindole-2-carboxylic acid. The resolved acids are useful intermediates in the preparation of a class of antihypertensive agents known as angiotensin converting enzyme (ACE) inhibitors. Such ACE inhibitors which are derivatives of 2,3-dihydroindole-2-carboxylic acid are described in U.S. Pat. No. 4,303,583, issued Dec. 1, 1981.

The inventive process for separating the optical enantiomers of (+)-2,3-dihydroindole-2-carboxylic acid comprises:

(a) combining the (+)-2,3-dihydroindole-2-carboxylic acid with (+) or (−)-ephedrine as the resolving agent in a resolution solvent;

(b) crystallizing out and isolating from said solution the (+)-ephedrine (+)-acid or (−)-ephedrine (−)-acid salt; and (c) regenerating the (+) or (−)-acid from the crystallized salt.

Suitable resolution solvents are acetonitrile, isopropanol, acetone or ethyl acetate, of which acetonitrile is preferred. A preferred process utilizes (+)-ephedrine as the resolving agent in order to isolate the (+)-2,3-dihydroindole-2-carboxylic acid.

In carrying out chemical resolutions of racemates, the purity of the initial crystalline product is crucial to the resolution and is dependent on the resolving agent, the solvent, and the reaction conditions. Although various optically active amine resolving agents, such (+) and (−)-amphetamine, dehydroabietylamine, (−)-α-methylbenzylamine, (−)-α-(2-naphthyl)ethylamine, (+)-α-(1-naphthyl)ethylamine, (+) and (−)-tetrahydrofurfurylamine, (−)-2-aminobutanol, and (+)-threo-2-amino-1-phenyl-1,3-propanediol, gave crystalline salts, only the (+) and (−)-ephedrine salts were of sufficient optical purity to afford complete separation of the enantiomers. Formation of the crystalline diastereomeric salt is achieved by admixture in solution of approximately equal molar quantities of the racemic acid with the (+) or (−)-ephedrine resolving agent (depending upon which resolved acid is desired) in an inert organic solvent. Recrystallization of the initially precipitated salt may be effected from acetonitrile, a lower alkanol (e.g. methanol, ethanol, or isopropanol), a lower alkyl ester (e.g. methyl or ethyl acetate), or a lower alkyl ketone (e.g. acetone or methyl ethyl ketone), which may be admixed with ether. ("Lower alkyl" refers to hydrocarbons having 1-3 carbon atoms). Recrystallization of the resolved acid may be effected from water or acetonitrile. The crystalline resolved acids obtained by crystallization from water are variously hydrated.

Regeneration of the resolved acid from the ephedrine-acid salt is effected by treatment of the salt with aqueous acid or by use of an ion-exchange resin. It will be recognized by the art-skilled organic chemist that the resolved acid is capable of forming a hydrochloride. Therefore, carefully controlled conditions must be employed to obtain the resolved acid from the pure ephedrine-acid salt via the route involving treatment with aqueous acid. In general, care must also be taken to prevent aerial oxidation of the 2,3-dihydroindole-2-carboxylic acid to the corresponding indole acid, which destroys the optical center.

The (+)-2,3dihydroindole-2-carboxylic acid to be resolved may be obtained as described by E. J. Corey et al., Journal of the American Chemical Society, 92, 2476, at 2480–1 (1970), or by other methods known in the art.

The following examples further illustrate the manner of carrying out the inventive processes described herein.

EXAMPLE 1

(+)-2,3-Dihydroindole-2-Carboxylic Acid

Racemic 2,3-dihydroindole-2-carboxylic acid (4.442 g., 0.0272 m.) was dissolved in boiling acetonitrile (272 ml.) and filtered from a small amount of insoluble residue. To this clear solution was added (+)-ephedrine (4.50 g., 0.0272 m.) in acetonitrile (20 ml.). The solution was allowed to stand without disturbance for 16 hr. and the precipitated needles filtered, washed with acetonitrile, then ether, and dried to provide (+) acid-(+)-ephedrine salt (1.615 g., m.p. 151°–153° C.); $[\alpha]_D^{26} = +47.1°$ (c=1, Chf). In prior runs, recrystallization of precipitated salt resulted only in loss of yield, not improvement in quality. This yield is 36.1% theory. A resin column (160 mm. in a 2.5 cm. glass column) was prepared by washing Bio-Rex-70, sodium form (100–200 mesh) with 10% aq. HCl, then distilled water until neutral. The salt was then dissolved in distilled water (50 ml.) and applied to the column which was then washed with distilled water (500 ml.). The water was then evaporated at room temperature using a dry ice condenser and the crystalline residue was freed from residual solvent on an oil pump to provide the (+)-acid, I-7629-57H (0.750 g., m.p. 160°–163° C., 33.8% yield; $[\alpha]_D^{26.5} = +27.7°$ (c=1, DMF).

EXAMPLE 2

(−)-2,3-Dihydroindole-2-Carboxylic Acid

In exactly like fashion, but employing (−)-ephedrine, there was obtained (−)-2,3-dihydroindole-2-carboxylic (−)-ephedrine salt (1.54 g.), m.p. 151°–153° C.; $[\alpha]_D^{26} = -51.4°$ (c=1, Chf) and then in turn the (−)-acid (0.725 g.), m.p. 159°–161° C., 32.6% yield, $[\alpha]_D^{26.5} = -30.7°$ (c=1, DMF).

EXAMPLE 3

(+)-2,3-Dihydroindole-2-Carboxylic Acid (+)-Ephedrine Salt

The (+)-2,3-dihydroindole-2-carboxylic acid (8.88 g., 0.0544 m.), and (+)-ephedrine (9.0 g., 0.0544 m.) were dissolved in 300 ml. acetonitrile and the slightly cloudy solution gravity filtered. The clear solution was stirred magnetically after seeding for 1.5 hr. The crude salts were filtered and dried over $P_2O_5$ to provide two crops: (1) 6.70 g., m.p. 134°–140° C. and (2) 0.800 g., m.p. 125°–131° C. The combined crops were recrystallized with seeding from acetonitrile (200 ml.) and filtered (3.5 hr.) to provide the pure salt 4.575 g., m.p. 153°–155° C. (51% yield). The salt should be protected from moist air and not washed.

Analysis for: $C_{19}H_{24}N_2O_3$: Calculated: C, 69.45; H, 7.37; N, 8.53; Found: C, 69.07; H, 7.27; N, 8.45.

$[\alpha]_D^{26} = +51.6°$ (c=1, Chf)—NMR and IR are compatible, the former indicating one acid to one amine.

EXAMPLE 4

(+)-2,3-Dihydroindole-2-Carboxylic Acid

The (+)(+) salt (1.85 g., m.p. 149°–152° C.) in 10 ml. H$_2$O, after warming, was adjusted to pH=4.0 with dropwise addition of 10% aqueous HCl and the precipitated solid filtered, washed with ice water and dried (P$_2$O$_5$ 18 hr.). Merck Index states, "1 gram l-ephedrine·HCl dissolves in 3 ml. of H$_2$O. 1 gram l-ephedrine sulfate dissolves in 1.5 ml. of H$_2$O". The isolated (+) acid is 0.610 g., m.p. 155°–158° C.; $[\alpha]_D^{26} = +35.3°$ (c=1, DMF).

EXAMPLE 5

(+)-2,3-Dihydroindole-2-Carboxylic Acid

A sample of this material isolated from a previous resolution was recrystallized from acetonitrile to provide anhydrous material, m.p. 167°–169° C., $[\alpha]_D^{24} = +32.01°$ (c=1, DMF).

Analysis for: C$_9$H$_9$NO$_2$: Calculated: C, 66.25; H, 5.56; N, 8.59; Found: C, 65.77; H, 5.45; N, 8.62.

NMR and IR are compatible.

EXAMPLE 6

(−)-2,3-Dihydroindole-2-Carboxylic Acid

A sample of this material isolated from a previous resolution was recrystallized from acetonitrile to provide anhydrous material, m.p. 162°–164° C., $[\alpha]_D^{24} = -34.7°$ C. (c=1, DMF).

Analysis for: C$_9$H$_9$NO$_2$: Calculated: C, 66.25; H, 5.56; N, 8.59; Found: C, 66.03; H, 5.43; N, 8.53.

NMR and IR are compatible.

EXAMPLE 7

(+)-2,3-Dihydroindole-2-Carboxylic Acid

Initial precipitation using (+)-acid (8.88 g., 0.0544 m.), (+)-ephedrine (9.00 g., 0.0544 m.) and CH$_3$CN (300 ml.) as in Example 3 provided the crude salt, 9.825 g., m.p. 130°–145° C. Recrystallization from CH$_3$CN (200 ml.) and standing for 2½ days gave the pure salt, 5.09 g., m.p. 149°–152° C.; $[\alpha]_D^{26} = +50.04°$ (c=1, Chf). Examination of the mother liquors and regeneration did not provide any resolved acid. This salt was dissolved in H$_2$O (25 ml.), chilled in an ice bath with stirring and, using a pH meter, taken to exactly pH=4 by dropwise addition of 10% aqueous HCl. After stirring for ½ hr. the precipitated solid was filtered, washed with ice H$_2$O and dried over P$_2$O$_5$ to provide the product, 2.33 g., m.p. 145°–148° C.; $[\alpha]_D^{26} = 28.9°$ (c=1, DMF). This is 98.0% yield from salt, 52.5% yield overall.

What is claimed is:

1. A process for separating the optical enantiomers of (±)-2,3-dihydroindole-2-carboxylic acid which comprises:
   (a) combining the (±)-2,3-dihydroindole-2-carboxylic acid with (+) or (−)-ephedrine as the resolving agent in a resolution solvent;
   (b) crystallizing out and isolating from said solution the (+)-ephedrine (+)-acid salt or the (−)-ephedrine (−)-acid salt; and
   (c) regenerating the (+) or (−)-acid from the crystallized salt.

2. A process according to claim 1 wherein the resolution solvent is selected from a group consisting of acetonitrile, isopropanol, acetone or ethyl acetate.

3. A process according to claim 1 wherein the resolution solvent is acetonitrile.

4. A process according to claim 1 wherein (+)-ephedrine is used as the resolving agent and final product is therefore the (+)-acid.

* * * * *